(12) United States Patent
Abele et al.

(10) Patent No.: US 7,907,336 B2
(45) Date of Patent: Mar. 15, 2011

(54) SURGICAL MICROSCOPE HAVING AN ILLUMINATING ARRANGEMENT

(75) Inventors: Alfons Abele, Schwäbisch Gmünd (DE); Peter Reimer, Ellwangen (DE); Anja Seiwert, Aalen (DE); Fritz Strähle, Heubach (DE); Franz Merz, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 407 days.

(21) Appl. No.: 12/155,166

(22) Filed: May 30, 2008

(65) Prior Publication Data

US 2008/0297892 A1 Dec. 4, 2008

(30) Foreign Application Priority Data

May 31, 2007 (DE) .......................... 10 2007 025 606
Aug. 29, 2007 (DE) .......................... 10 2007 041 003

(51) Int. Cl.
*G02B 21/06* (2006.01)
(52) U.S. Cl. ....................................................... 359/385
(58) Field of Classification Search .......... 359/376–378, 359/385, 389
See application file for complete search history.

(56) References Cited

U.S. PATENT DOCUMENTS

| | | | | |
|---|---|---|---|---|
| 3,769,963 A * | 11/1973 | Goldman et al. | ............ | 600/476 |
| 4,682,595 A * | 7/1987 | Hoerenz et al. | .................... | 606/4 |
| 4,715,704 A | 12/1987 | Biber et al. | | |
| 4,932,774 A * | 6/1990 | Takagi et al. | ................. | 351/221 |
| 5,126,877 A | 6/1992 | Biber | | |
| 5,748,367 A * | 5/1998 | Lucke et al. | .................. | 359/385 |
| 5,760,952 A * | 6/1998 | Koetke | .......................... | 359/389 |
| 5,838,491 A * | 11/1998 | Gartner et al. | ................ | 359/385 |
| 6,011,647 A | 1/2000 | Geschwentner | | |
| 6,236,502 B1 | 5/2001 | Kitajima | | |
| 6,392,797 B2 * | 5/2002 | Strahle | ........................ | 359/389 |
| 6,624,932 B2 | 9/2003 | Koetke | | |
| 6,816,304 B2 * | 11/2004 | Nakamura et al. | ............ | 359/388 |
| 7,307,785 B2 | 12/2007 | Obrebski et al. | | |
| 7,443,579 B2 * | 10/2008 | Kitajima | ........................ | 359/388 |
| 2001/0040726 A1 * | 11/2001 | Sander | .......................... | 359/387 |
| 2005/0128574 A1 | 6/2005 | Reimer et al. | | |
| 2006/0232855 A1 * | 10/2006 | Nakamura et al. | ............ | 359/385 |
| 2007/0263173 A1 | 11/2007 | Reimer et al. | | |
| 2009/0273757 A1 | 11/2009 | Merz et al. | | |

FOREIGN PATENT DOCUMENTS

| | | |
|---|---|---|
| DE | 196 11 044 | 9/1996 |
| DE | 20 2004 019 849 | 2/2005 |
| EP | 1 410 754 | 4/2004 |

OTHER PUBLICATIONS

"Abc Der Optik", Edition Leipzig, Werner Dausien, 1961, p. 83, Hanau/Main, Germany.
European Search Report (Jul. 31, 2008) (Translation into English).

* cited by examiner

*Primary Examiner* — Mark Consilvio
(74) *Attorney, Agent, or Firm* — Walter Ottesen (57) ABSTRACT

A surgical microscope (100) has an illuminating arrangement (110) which can guide illuminating light to the object region (105) with a first illuminating beam path (111) and with a second illuminating beam path (112). A light exit unit is provided in the first illuminating beam path (111). An illuminating field diaphragm is mounted in the second illuminating beam path. The first illuminating beam path (111) has an illuminating optic which images the light exit plane of the light exit unit or a plane conjugated to the light exit plane into a first image plane (350). An illuminating optic is provided in the second illuminating beam path (112) and this illuminating optic images the illuminating field diaphragm into a second image plane (250) different from the first image plane.

29 Claims, 10 Drawing Sheets

SURGICAL MICROSCOPE HAVING AN ILLUMINATING ARRANGEMENT

CROSS REFERENCE TO RELATED APPLICATIONS

This application claims priority of German patent application nos. 10 2007 025 606.1 and 10 2007 041 003.6, filed May 31, 2007 and Aug. 29, 2007, respectively, the entire contents of both applications being incorporated herein by reference.

FIELD OF THE INVENTION

The invention relates to a surgical microscope having an illuminating arrangement which can provide illuminating light for the object region with a first illuminating beam path and with a second illuminating beam path. A first light exit unit is provided in the first illuminating beam path to make available light and an illuminating field diaphragm is arranged in the second illuminating beam path. The first illuminating beam path includes an illuminating optic which images the light exit plane of the first light exit unit or a plane conjugated to this light exit plane into a first image plane.

BACKGROUND OF THE INVENTION

A surgical microscope of the kind described above is known from U.S. Pat. No. 5,126,877. This surgical microscope comprises an illuminating arrangement wherein illuminating light is made available via the exit end of a light conductor perpendicularly to the optical axis of the microscope main objective. This illuminating light having a beam path, which is parallel to the optical axis of the microscope main objective, is deflected to the microscope main objective via a first deflecting element and a second deflecting element on the side of the microscope main objective facing away from the object region. The illuminating light is guided with a first beam path through the microscope main objective to the object region and with a second beam path. The first beam path runs axis-near to the optical axes of the viewing beam paths of the microscope and the second beam path illuminates the object region with inclined light and has an axis-far course with reference to the optical axes of the viewing beam paths of the surgical microscope. The illuminating field corresponds to the image of an illuminating field diaphragm in the object region with the diaphragm being arranged at the exit end of the light conductor and the image of the illuminating field diaphragm being generated by means of the illuminating optic.

With the use of surgical microscopes in surgical procedures, different requirements are placed on the illumination of the area of surgery depending upon the medical specialty. In surgical procedures in ENT surgery and neurosurgery, the area of surgery is illuminated with axis-near inclined illumination with reference to the viewing beam paths so that especially narrow, deep body cavities can be illuminated without the formation of shadows. For microsurgical procedures on the eye, illuminating light reflected diffusely from the retina is used which appears to a surgeon examining the lens of the patient eye as red transmitted light in order to make visible transparent structures in the anterior region of the patient eye.

In ophthalmologic surgical procedures, it is advantageous when a surgeon has the possibility in a surgical microscope to illuminate the area of surgery with illuminating light at different angles with reference to the optical axes of the viewing beam paths in order to be able to adjust the contrast of the viewed image in this manner.

United States published patent application US 2005/0128574 A1 describes an illuminating arrangement for an ophthalmologic surgical microscope which has an illuminating beam path which effects an image of the illuminating pupil of the illuminating arrangement on the retina of a patient eye under examination.

United States published patent application US 2007/0263173 A1 discloses a surgical microscope having an illuminating arrangement wherein a beam splitter element is provided in the stereoscopic viewing beam paths in order to coaxially superpose illuminating light onto the viewing beam paths with this illuminating light being directed to the object region through the microscope main objective.

International patent application having publication number WO 2007/110207 discloses a surgical microscope having an illuminating arrangement which provides illuminating light with an illuminating beam path which is guided through the microscope main objective to the object region. The illuminating arrangement includes a Köhler illuminating optic. A reflex diaphragm is mounted in the illuminating beam path. The reflex diaphragm effects a shading of such illuminating light which would get into the viewing beam paths of the surgical microscope because of reflections on the microscope main objective. In this way, disturbing reflections in the viewed image of the surgical microscope can be avoided.

U.S. Pat. No. 4,715,704 discloses an ophthalmologic surgical microscope having an illuminating arrangement which includes a retina protective diaphragm pivotable into and out of the illuminating beam path. The retina protective diaphragm is configured as an annularly-shaped diaphragm. In the pivoted-in state, the annularly-shaped diaphragm is disposed in a plane conjugated to the object plane of the surgical microscope and blocks illuminating light or attenuates such illuminating light which could otherwise reach the retina through the iris of a patient eye.

U.S. Pat. No. 6,011,647 discloses a surgical microscope which comprises an illuminating arrangement which makes possible to illuminate the object region in different configurations for the illuminating light. The illuminating arrangement can, on the one hand, make available illuminating light via an illuminating field diaphragm which is imaged into the object region via the microscope main objective. On the other hand, the illuminating arrangement can illuminate the object region with illuminating light in a configuration wherein the coiled filaments of a lamp or the exit end of a light conductor are imaged into the object region through the microscope main objective.

German utility model registration 20 2004 019 849 U1 discloses a surgical microscope which makes possible the illumination of an object region with differently configured illuminating light through the microscope main objective. In a first configuration for illuminating light, an illuminating field diaphragm is imaged into the object region via the microscope main objective corresponding to U.S. Pat. No. 6,011,647. Corresponding to the second configuration, the illuminating light passes through a diffuser which is arranged at a light source imaged into the object region.

SUMMARY OF THE INVENTION

It is an object of the invention to provide a surgical microscope which is suited for use in ophthalmology and makes possible to make visible transparent structures in the anterior section of a patient eye with good contrast.

The surgical microscope of the invention is for examining a region of an object. The surgical microscope comprises an illuminating arrangement including: a first illuminating beam path for providing illuminating light to the region of the object; a second illuminating beam path for providing illuminating light to the region of the object; a first light exit unit for making light available in the first illuminating beam path; an illuminating field diaphragm arranged in the second illuminating beam path; the first light exit unit defining a light exit plane; a first illuminating optic disposed in the first illuminating beam path for imaging the light exit plane or a plane conjugated to the light exit plane into a first image plane; and, a second illuminating optic disposed in the second illuminating beam path for imaging the illuminating field diaphragm into a second image plane different from the first image plane.

In this way, a surgical microscope is provided wherein a large illuminating field is ensured with clean boundaries and wherein, simultaneously, a light-intensive red reflex can be generated at an examined patient eye.

In a further embodiment of the invention, the first illuminating beam path is guided to the object region with an axis-near course relative to at least one optical axis of the viewing beam path of the surgical microscope. In this way, a red reflex with good homogeneity can be generated at a patient eye.

In a further embodiment of the invention, the second illuminating beam path is guided to the object region with an axis-far course relative to at least one optical axis of the surgical microscope. In this way, a good plasticity of an image of the object region is effected in the surgical microscope because the illuminating light, which incidents at an inclination, causes shadows to form at structures in the object region.

In a further embodiment of the invention, the first illuminating beam path and/or the second illuminating beam path pass through the microscope main objective in the surgical microscope. In this way, a large clear work area is made possible between the microscope main objective and the object region.

In a further embodiment of the invention, a first and a second deflecting element are provided in the surgical microscope which direct axis-near and axis-far illuminating light, respectively, through the microscope main objective to the object region. In this way, with reference to the optical axis of the microscope main objective, lateral in-coupling of illuminating light into the system is made possible.

In a further embodiment of the invention, the first deflecting element is configured as a partially transmissive mirror through which an illuminating beam path of the surgical microscope passes. The partially transmissive mirror can especially be configured as a geometric or physical beam splitter. In this way, a beam path for the illuminating light can be guided without vignetting close to the viewing beam paths of the surgical microscope.

In a further embodiment of the invention, the first deflecting element functions to coaxially superpose axis-near illuminating light onto a stereoscopic viewing beam path, preferably a left and a right stereoscopic viewing beam path. In this way, illuminating light is guided coaxially to the viewing beam path onto the object region. Accordingly, in ophthalmology, an especially light-intensive and homogeneous red reflex can be achieved at a patient eye.

In a further embodiment, a second deflecting element is provided which directs illuminating light through the microscope main objective to the object region. In this way, a compact configuration of the surgical microscope is made possible.

In a further embodiment of the invention, the second image plane (in which the image of the illuminating field diaphragm lies in the second illuminating beam path) is coincident with the object plane of the surgical microscope. In this way, a clean boundary of illuminating field in the object region is achieved.

In a further embodiment, the second illuminating field diaphragm is configured as a diaphragm having a variable, especially adjustable diaphragm opening. In this way, the size of the illuminating field in the object region can be adjusted.

In a further embodiment of the invention, a further diaphragm is arranged at the illuminating field diaphragm. Preferably, this additional diaphragm is configured as a retina protective diaphragm. In this way, the load on the retina with illuminating light can be reduced or prevented during ophthalmologic surgical procedures.

In a further embodiment of the invention, an aperture diaphragm is arranged in the second illuminating beam path. Preferably, this aperture diaphragm is configured so as to be adjustable. With this measure, the brightness of the illuminating field can be varied in the surgical microscope without it being necessary to provide a control of a light source power.

In a further embodiment of the invention, a diaphragm having a variable, especially adjustable diaphragm opening is configured in the first illuminating beam path in order to control the quantity of light in the beam path. In this way, the brightness of the red reflex in ophthalmology can be changed without control of a light source power.

In a further embodiment of the invention, a common user-actuable operator-controlled element is provided for adjusting the diaphragm in the second illuminating beam path and/or the aperture diaphragm and/or the diaphragm in the first illuminating beam path. In this way, an ergonomically advantageously manipulable surgical microscope is provided.

In a further embodiment of the invention, the user-actuable operator-controlled element is configured as a rotational knob. In this way, a reliable setting of diaphragm configurations is made possible. Defective or faulty actuations can be substantially precluded which would have as a consequence damage of a patient eye by the illuminating light.

In a further embodiment of the invention, the rotational knob is coupled to a shaft unit which is operatively connected via a first control cam as well as a first output unit to the diaphragm in the first illuminating beam path. The shaft unit is also operatively connected via a second control cam as well as a second output unit to the adjustable diaphragm in the second illuminating beam path. The shaft unit is also operatively connected via a third control cam as well as a third output unit to the aperture diaphragm. In this way, an especially small structural configuration of the illuminating arrangement is made possible and a reliable operation of the surgical microscope is ensured without electric drives.

In a further embodiment of the invention, a common light source is assigned to the first illuminating beam path and to the second illuminating beam path. In this way, a cost-favorable construction for a surgical microscope having an illuminating arrangement is achieved.

In a further embodiment of the invention, in the surgical microscope, a light conductor with a branching junction is provided which supplies the light of the common light source to the first illuminating beam path and to the second illuminating beam path. In this way, in the surgical microscope, the light source can be mounted at a distance from the optic of the surgical microscope.

In a further embodiment of the invention, the light conductor has a first light exit unit and a second light exit unit. In this way, it is possible to simultaneously make available illuminating light for an axis-near illuminating beam path and for an axis-far illuminating beam path while using a single light source.

In a further embodiment of the invention, a first illuminating pupil and a second illuminating pupil are configured on the first light exit unit. In this way, an optimized red reflex illumination can be achieved for both stereoscopic viewing beam paths of a surgical microscope.

In a further embodiment of the invention, a single illuminating pupil is configured on the second light exit unit. In this way, a homogeneous illuminating field is provided in the object region of the surgical microscope.

In a further embodiment of the invention, a reflex diaphragm is provided in the first illuminating beam path of the surgical microscope and this reflex diaphragm shades or occludes illuminating rays which cause disturbing scattering light in the viewing beam paths of the surgical microscope with the scattering light being caused by reflections at optical elements in the surgical microscope, especially, reflections at the microscope main objective. In this way, the contrast of the image visible for a viewer in the binocular tube of the surgical microscope can be maximized.

In a further embodiment of the invention, the reflex diaphragm in the first illuminating beam path of the surgical microscope is mounted in such a manner that no viewing rays are masked in the surgical microscope and no cropping of the image of the illuminating field diaphragm takes place in the second image plane by the reflex diaphragm. In this way, a light intense viewing image is effected in the surgical microscope wherein no disturbing reflections take place. The illuminating field is uniformly illuminated in all regions.

In a further embodiment of the invention, the illuminating arrangement is so designed in the surgical microscope that at least one illuminating spot (preferably a first illuminating spot and a second illuminating spot) having a diameter in the range of 0.5 mm to 1.5 mm can be generated on the retina of an ideal patient eye with the illuminating light from the first illuminating beam path. In this way, a red reflex is generated at the patient eye which is visible with excellent contrast in the surgical microscope.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
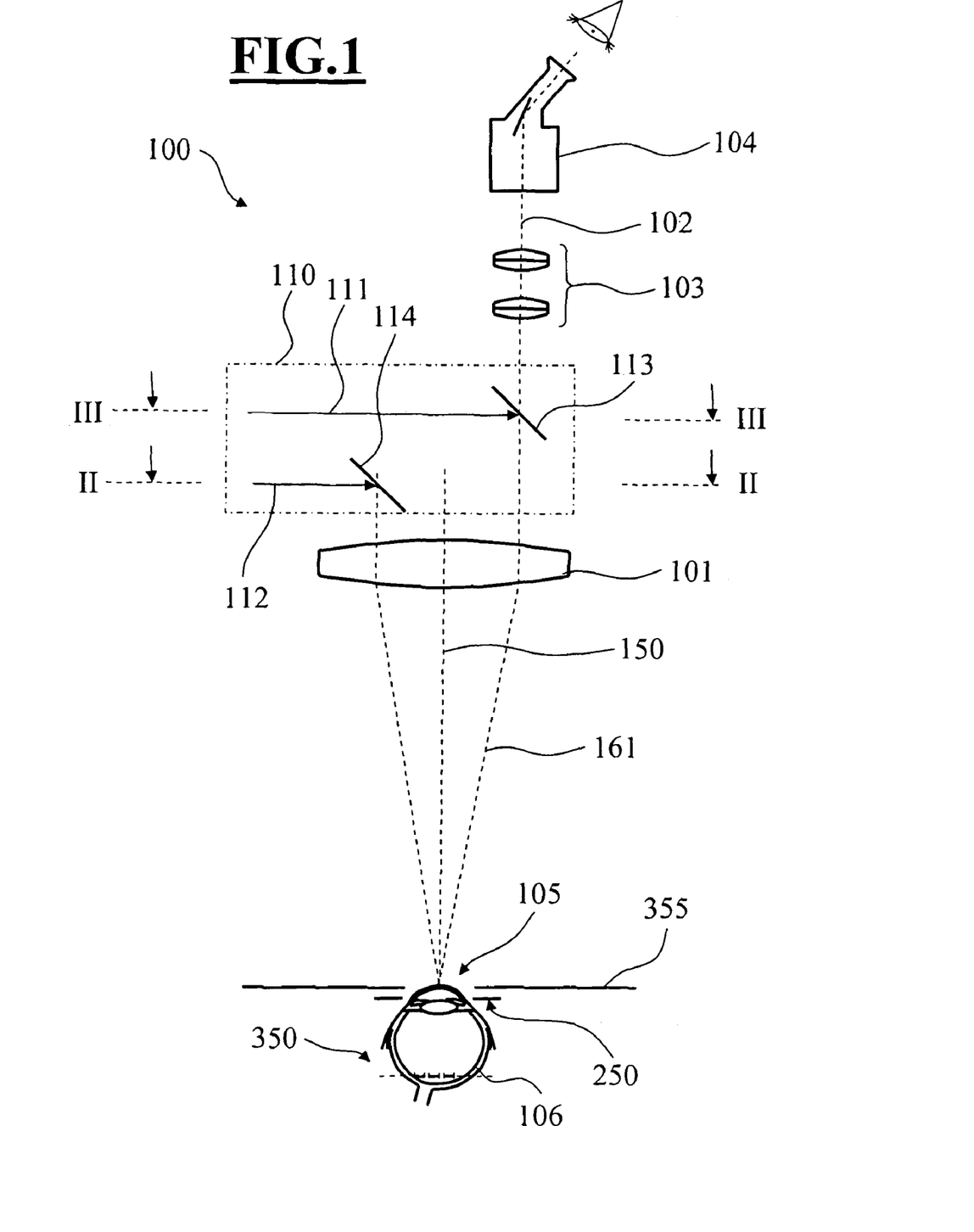
FIG. 1 shows a schematic section of a first surgical microscope having an illuminating arrangement which provides a first illuminating beam path with axis-near illuminating light for red reflex illumination and a second illuminating beam path with axis-far illuminating light for surround illumination with each illuminating beam path being guided through the microscope main objective of the surgical microscope.

The surgical microscope 100 shown in FIG. 1 has a microscope main objective 101 defining an optical axis 150 and through which a stereoscopic viewing beam path 102 passes. The left component beam path of the stereoscopic viewing beam path 102 is shown in FIG. 1. This component beam path has an optical axis 161. The surgical microscope 100 permits a viewer to examine an object region 105 in an object plane 355 via a magnification system 103 and a binocular tube 104. The surgical microscope 100 is designed as an ophthalmologic surgical microscope and is especially suited for examining an eye 106 of a patient.

The surgical microscope 100 comprises an illuminating arrangement 110. With reference to the stereoscopic viewing beam path 102, the illuminating arrangement 110 provides an illuminating beam path 111 for axis-near illumination of the object region and an illuminating beam path 112 for the axis-far illumination of the object region.

The illuminating arrangement 110 includes a mirror 113 which is partially transmissive for light and which functions as a first deflecting element in order to superpose illuminating light on the stereoscope viewing beam path 102 axis-near and coaxially to the optical axis of the stereoscopic viewing beam path. The illuminating arrangement 110 includes a mirror 114 as a second deflecting element which directs illuminating light through the microscope main objective 101 with an axis-far course to the object region 105, that is, at an angle to the optical axis of the viewing beam paths.

Figure 2:
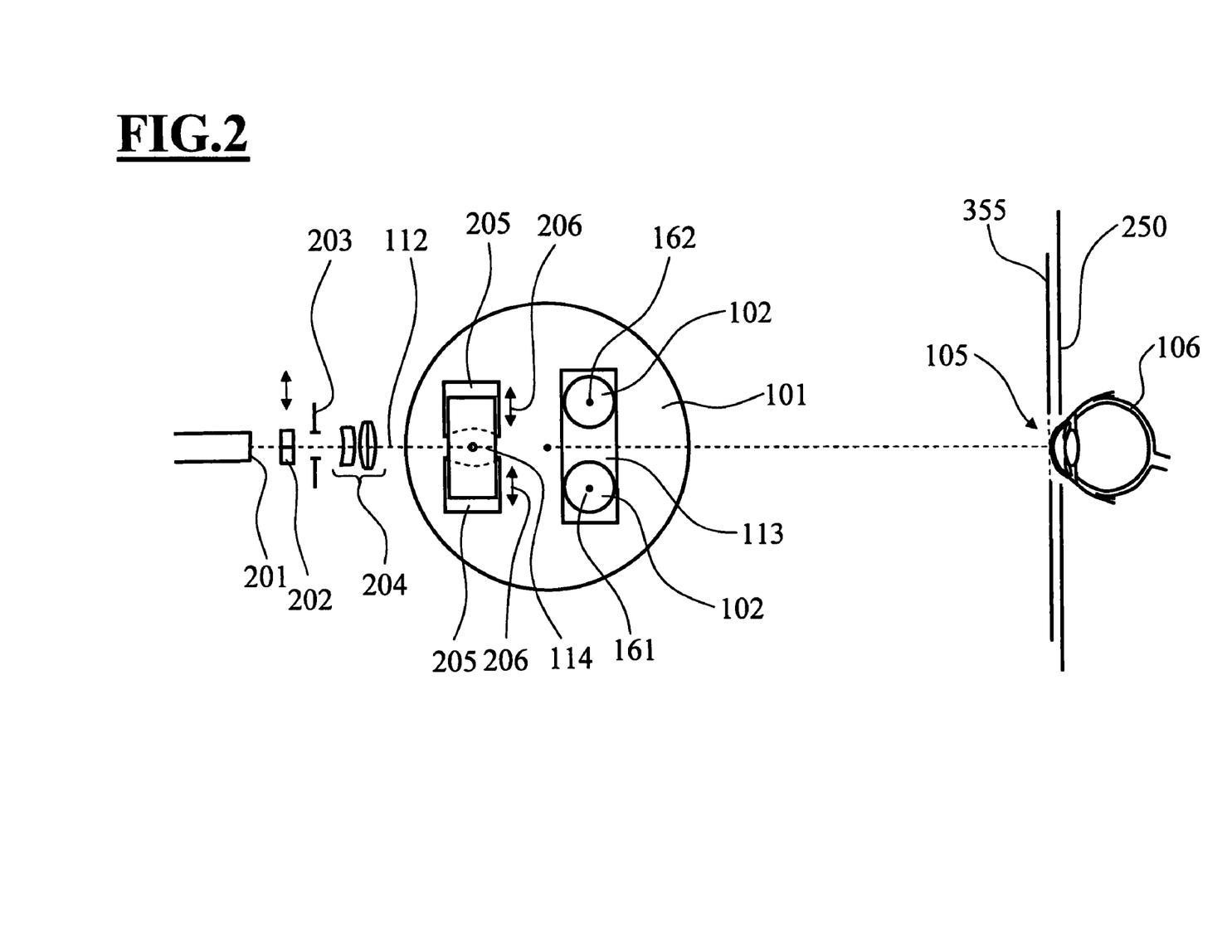
FIG. 2 is a schematic section view taken along line II-II of the surgical microscope of FIG. 1 having an illuminating beam path for surround illumination.

FIG. 2 shows a section taken along line II-II of FIG. 1. The same reference numerals are used in FIG. 2 as in FIG. 1 insofar as they are applied to the same component assemblies or items.

The stereoscopic viewing beam path 102 passes through the microscope main objective 101 with a left component beam path and a right component beam path having respective optical axes 161 and 162. The microscope main objective 101 has a focal length of f=200 mm. A favorable focal length for the main objective of the surgical microscope is, however, also the focal length f=175 mm or f=225 mm.

In order to guide axis-far illuminating light to the object region, the light is guided from a light exit unit in the form of a light conductor exit end 201 via an adjustable diaphragm 202 and an illuminating field diaphragm 203 through an illuminating optic 204 to the mirror 114. The mirror 114 directs the light through the microscope main objective 101 to the object region 105.

The diaphragm 202 can be adjusted as a retina protective diaphragm. In this setting, an annular diaphragm is disposed in the illuminating beam path 112 as described in U.S. Pat. No. 4,715,704 incorporated herein by reference.

The illuminating field diaphragm 203 is imaged into an image plane 250. This image plane 250 lies close to but not precisely in the object plane 355 of the surgical microscope 100 of FIG. 1. In this way, a limiting of the illuminating field in the object plane results which, in its peripheral region, is not abrupt but passes gradually from bright to dark. This ensures a pleasant viewing impression for a viewer in the ocular also at the peripheral region of the illuminating field. It should be noted that basically also a sharp imaging of the illuminating field diaphragm in the object plane of a surgical microscope can be provided. This measure is, however, also associated with the disadvantage that the light passthrough opening of the illuminating field diaphragm (which often has mechanical defects because of manufacture) is imaged as a magnified image in the object plane of the surgical microscope where these defects are then visible.

If the diaphragm 202 is adjusted for operating as a retina protective diaphragm, illuminating light is prevented from reaching into the interior of the patient eye 106 to the ocular fundus where it may cause damage. The diaphragm 202 is imaged into the object region 105, that is, in the setting of the surgical microscope 100 shown in FIG. 1, the diaphragm 202 is imaged approximately onto the cornea of the patient eye 106. An adjustable diaphragm 205 is provided between the microscope main objective 101 and the mirror 114. This adjustable diaphragm 205 can be adjusted in correspondence to the double arrow 206 in order to clear or to block the illuminating beam path from the light conductor exit end 201. The diaphragm 205 can therefore be so adjusted that it can clear or block the illuminating beam path continuously or in steps.

Figure 3:
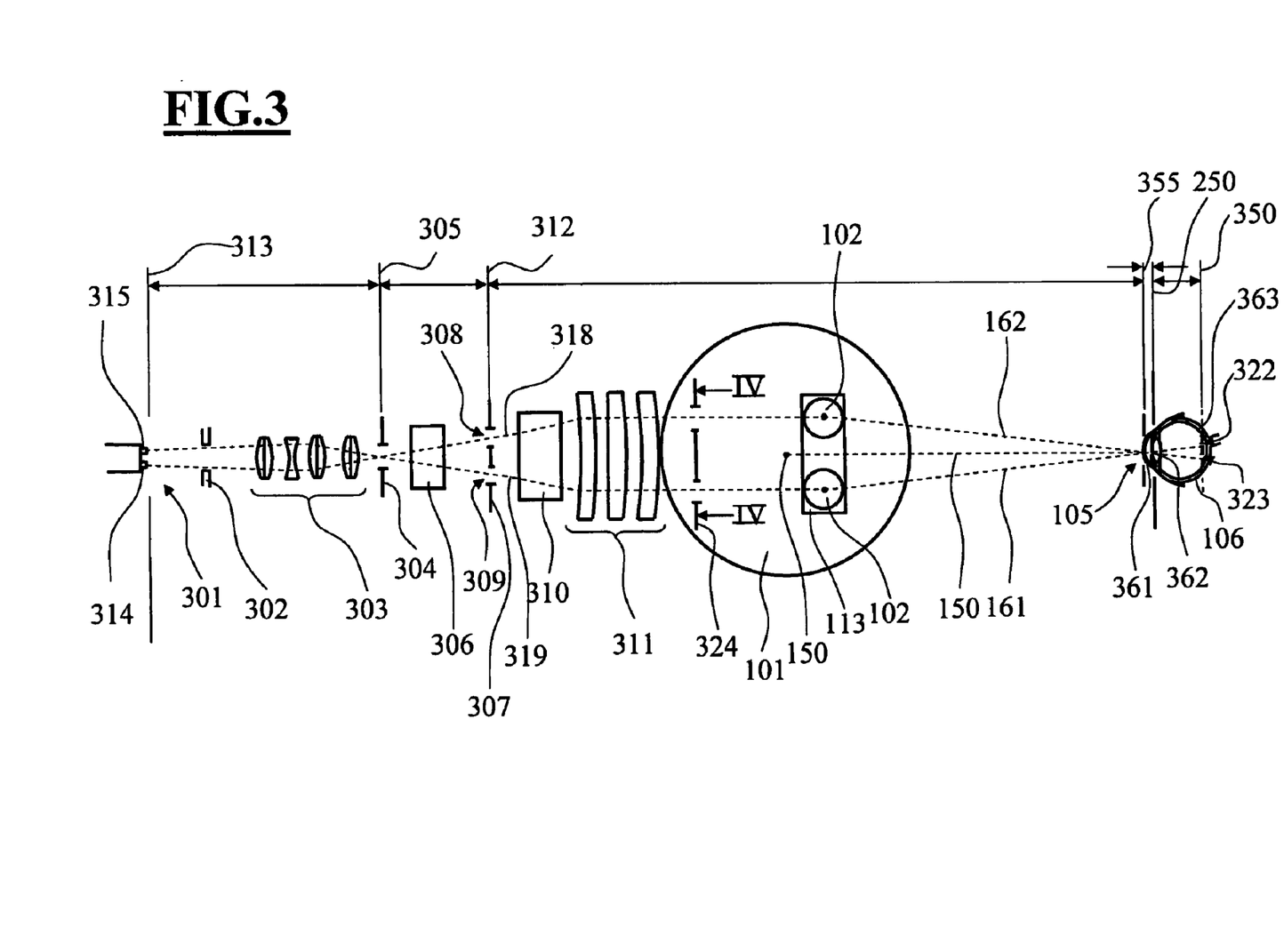
FIG. 3 is a schematic section view taken along line III-III of the surgical microscope of FIG. 1 having a first illuminating beam path for red reflex illumination.

FIG. 3 shows a schematic section view of the surgical microscope taken along line III-III of FIG. 1. The same reference numerals used in FIG. 1 are also used in FIG. 3 insofar as the component assemblies of the surgical microscope of FIG. 3 correspond to those component assemblies of FIG. 1.

In order to guide axis-near illuminating light to the object region 105, an illuminating field diaphragm 304 is illuminated with the light from a light exit unit in the form of a light conductor exit end 301 via an adjustable or closeable aperture diaphragm 302 and a first illuminating optic 303. This illuminating field diaphragm 304 is arranged in a plane 305. From the illuminating field diaphragm 304, the illuminating light is directed to a mirror element 310 with a folded illuminating beam path via a mirror element 306 and a double diaphragm 307 having two diaphragm openings 308 and 309. This mirror element 310 directs the illuminating light to the deflecting element 113 via a second illuminating optic 311 perpendicularly to the optical axis 150 of the microscope main objective 101 and through a reflection diaphragm 324. The reflection diaphragm 324 operates as a baffle for stray light and the deflecting element 113 is configured as a beam splitter through which the left and right stereoscopic viewing beam paths 102 of the surgical microscope pass. The deflecting element 113 directs the illuminating light to the object region 105 parallel to the optical axis 150 of the microscope main objective 101 and through the microscope main objective 101 coaxially to the stereoscopic viewing beam paths 102.

The double diaphragm 307 operates as an aperture diaphragm. The aperture diaphragm is arranged in a plane 312 which is conjugated to the light exit plane 313 of the light conductor exit end 301. At the light conductor exit end 301, a first light exit unit 314 having a first illuminating pupil and a second light exit unit 315 having a second illuminating pupil are formed. These first and second light exit units (314, 315) are imaged magnified by the first illuminating optic 303 into the plane 312 of the double diaphragm 307 having diaphragm openings 308 and 309.

Via the mirror elements (306, 310) and with the second illuminating optic 311, the illuminating field diaphragm 304 is imaged through the microscope main objective 101 into the image plane 250 in the object region 105. More specifically, the plane 305 of the illuminating field diaphragm 304 is conjugated to this image plane 250. In this way, a clean delimiting of the illuminating field in the object region results with the illuminating field being caused by this illuminating beam path.

The diaphragm openings (308, 309) of the double diaphragm 307 are imaged through the microscope main objective 101 and the patient eye 106 into an image plane 350 via the mirror element 310 and the second illuminating optic 311. The image plane 350 is different from the image plane 250 of the illuminating field diaphragm 304. The image plane 350 is thereby conjugated to the plane 312 of the double diaphragm 307 and to the light exit plane 313 of the light conductor exit end. The optical axes (318, 319) of the imaging beam path for the diaphragm openings (308, 309) of the double diaphragm 307 are passed with the deflecting element 113 into the optical axes (161, 162) of the left and right stereoscopic viewing beam paths 102.

This imaging beam path is parallel or essentially parallel between the microscope main objective 101 and the patient eye 106. More specifically, without the diffracting action of the cornea 361 and the lens 362 of the patient eye 106, the image plane 350 for the double diaphragm 307 lies at infinity, that is, the image plane 350 is spaced far from the focal plane (that is, the object plane 355 of the microscope main objective 101). It is possible that the corresponding imaging beam path for the double diaphragm 307 runs slightly expanded at the exit end of the microscope main objective 101. Then, without the diffracting action of the cornea 361 and the lens 362 of the patient eye 106, the image plane 350 is arranged on the side of the microscope main objective 101 facing away from the object and is of virtual nature. If the imaging beam path runs slightly convergent at the exit side of the main objective 101, the image plane 350 is real and is located on the side of the microscope main objective 101 facing toward the object.

If a patient eye 106 is examined with the surgical microscope, then the cornea 361 and the natural lens 362 in the eye cause the parallel or approximately parallel illuminating beam path to be bundled with the illuminating beam path running along the optical axis 161 and 162. For an emmetropic patient eye 106 adapted to infinity, the refractive power of the cornea 361 and the natural lens 362 have the consequence that the focus of the illuminating beam path lies on the retina 363 of the patient eye 106, that is, the image plane 350 is disposed at the retina 363 of the patient eye 106. An image of the double diaphragm 307 is then disposed on the retina 363 of the patient eye 106. In this way, a first illuminating spot 322 and a second illuminating spot 323 occur at the retina 363 of the patient eye 106.

The dimensioning of the size of the light exit units (314, 315) and their mutual distance as well as the dimensioning of the diaphragm openings (308, 309) and their mutual spacing in the double diaphragm 307 and the dimensioning of the imaging optic 311 in the illuminating beam path and the focal length of the microscope main objective 101 are so selected in the surgical microscope that, for the examination of an ideal patient eye, two illuminating spots (322, 323) arise on the retina on the optical axes (161, 162) of the viewing beam paths with the diameter of these illuminating spots lying in the range of 0.5 mm to 1.5 mm. The ideal patient eye corresponds with respect to its optical characteristics to those of the schematic eye of Gullstrand as set forth on page 83 of the text entitled "ABC der Optik", Edition Leipzig, Publisher Werner Dausien, Hanau/Main (1961). Here, small illuminating spots are especially favorable because they are the condition precedent for an especially contrast-rich red reflex image of the forward portion of a patient eye which is presented for a viewer in the ocular of the surgical microscope. The size of an illuminating spot on the ocular fundus should not, however, be too large. With increasing size of the illuminating spot on the ocular fundus, the contrast of the red reflex image of the anterior part of the patient eye decreases in the surgical microscope.

Especially small illuminating spots are achieved in that the double diaphragm 307 or the light exit plane 313 of the light conductor exit end 301 is imaged on the retina 363 of the patient eye 106, that is, when the image plane 350 lies on the retina 363, that is, on the ocular fundus of the patient eye 106, which is presented for a viewer in the ocular of the surgical microscope.

A spot size which is too small is, however, disadvantageous. If the spot size is too small, then the homogeneity of the red reflex deteriorates, that is, the red reflex becomes darker outwardly at its peripheral region. Furthermore, an illuminating spot which is too small on the retina presents the danger that the retina of the patient eye will become damaged because of the high irradiation intensity of the illuminating light at this location.

It is understood that the illuminating beam path for axis-near illuminating light need not necessarily be configured as folded when a correspondingly large structural volume is accepted. Furthermore, it is noted that the mirror elements 306 and 310 and the respective illuminating optics 303 and 311 can also be configured to have multiple pieces so that illuminating light, which is coupled into the left and right stereoscopic viewing beam paths, is guided via different mirrors and objectives.

Furthermore, it is noted that the light conductor exit end 301 can be mounted in plane 312 of the double diaphragm 307. With this measure, it is accepted that the illuminating beam path which exits from the light conductor exit end, effects an illuminating field in the object region which is not sharply delimited. The illuminating system can, however, be built in this way in an especially space-saving manner.

Figure 4:
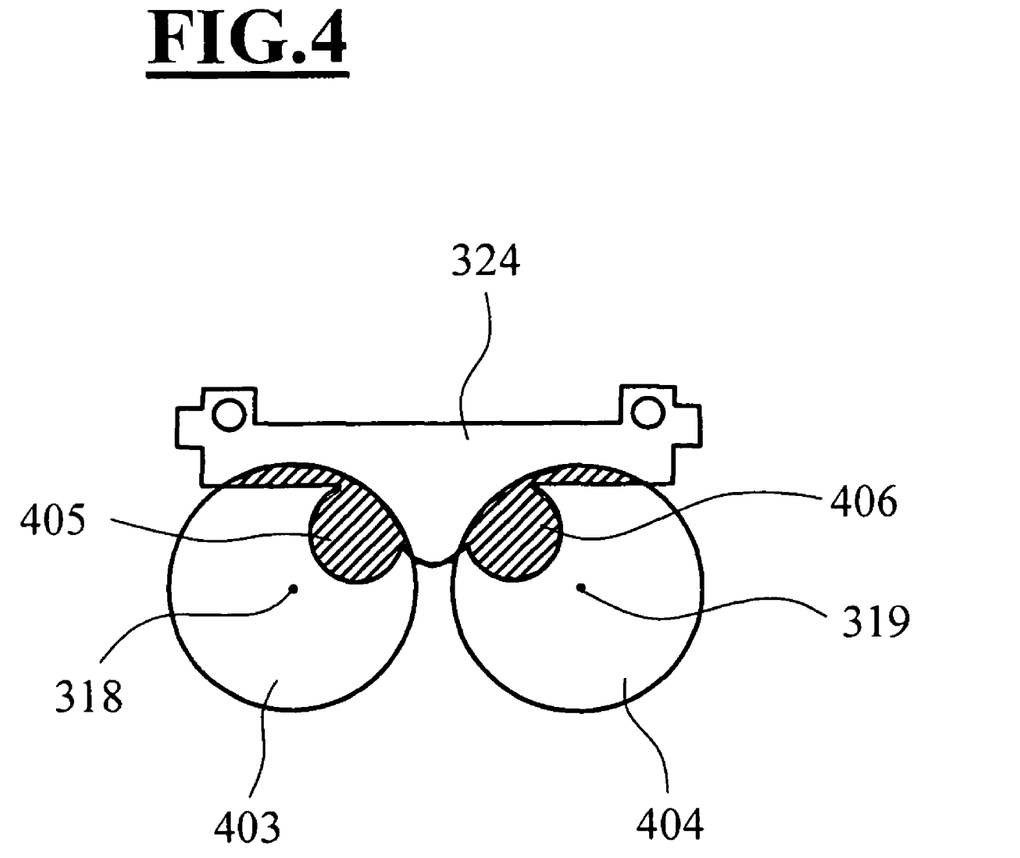
FIG. 4 is a reflex diaphragm in the first illuminating beam path for red reflex illumination.

FIG. 4 shows a section view of the reflex diaphragm 324 along line IV-IV of FIG. 3. At the reflex diaphragm 324, the illuminating beam path has an optical axis 318 and an optical axis 319 with cross-sectional areas 403 and 404. From the illuminating beam path, those illuminating rays are shaded in the regions 405 and 406 by means of the reflex diaphragm 324 which cause scattered light after deflection by the deflection element 113 because of reflections on the microscope main objective 101 in FIG. 1 with this scattered light being collected via the magnification system 103 in the surgical microscope 100 of FIG. 1 so that the viewing image, which is visible for a viewer in the binocular tube 104, is not affected.

Figure 5:
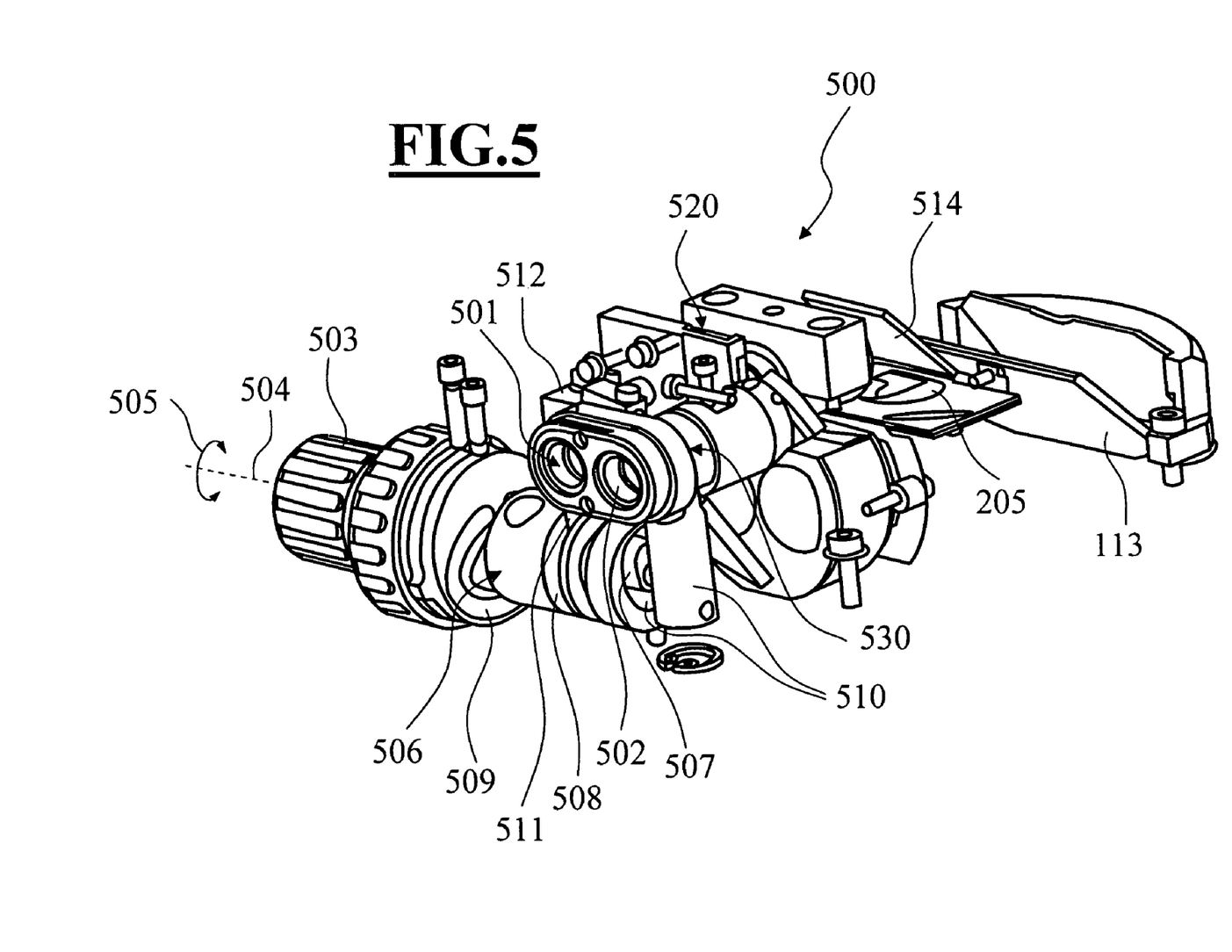
FIG. 5 is a three-dimensional view of a component assembly of the illuminating arrangement having a rotational knob.

FIG. 5 shows a three-dimensional view of a central unit 500 of the illuminating arrangement 110 of FIG. 1. The same reference numerals are used insofar as the component assemblies of the unit 500 are shown in FIG. 1, 2, 3 or 4. The unit 500 of the illuminating arrangement has a receptacle 501 for a light conductor end which provides light for axis-far illumination. The unit 500 includes a receptacle 502 for a light conductor end from which light exits for axis-near illuminating light.

In the unit 500, a rotational knob 503 is provided for adjusting the retina protective diaphragm 202 of FIG. 2 as well as the diaphragm 205 and the aperture diaphragm 302 of FIG. 3. The retina protective diaphragm 202 is arranged at reference numeral 520 and the aperture diaphragm 302 is arranged at reference numeral 530. The rotational knob 503 can be rotated about an axis 504 corresponding to the double arrow 505. The rotational knob 503 has a shaft 506 on which the following are formed: a first control cam 507, a second control cam 508, and a third control cam 509. The first control cam 507 is operatively connected to a first output unit 510 by means of which the diaphragm 302 of FIG. 3 can be adjusted. The second control cam 508 operates on a second output unit 511 in order to adjust the retina protective diaphragm 202 of FIG. 2. The third control cam 509 is operatively connected to a third output element 512 which controls the diaphragm 205 of FIG. 2.

Figure 6:
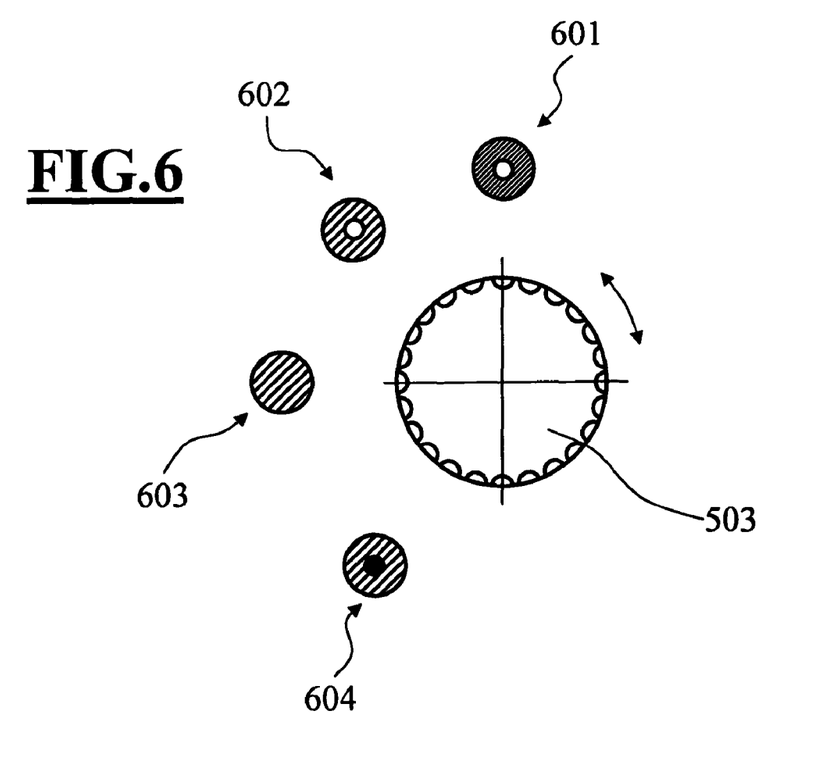
FIG. 6 is a schematic showing different settings of the rotational knob of the component assembly.

FIG. 6 shows various possible settings of the rotational knob 503 of FIG. 5. In the setting 601, the beam path for axis-far illuminating light is blocked and only axis-near illuminating light is conducted to the object region. By changing the setting of the rotational knob 503 from the position 601 into the position 602, the intensity of that illuminating radiation increases which, in the surgical microscope, is guided to the object region with an axis-far course with reference to the optical axis of the viewing beam path. In the setting 602, axis-near as well as axis-far illuminating light is made available. The rotational knob 503 can be moved further into the position 603. In this position 603, the beam path for axis-near illuminating light is interrupted and only axis-far illuminating light is conducted to the object region. Finally, a position 604 is possible for the rotational knob 503. In position 604 of the rotational knob, the beam path for axis-near illuminating light is interrupted. In this setting, illuminating light corresponding to the illuminating beam path for axis-far illuminating light is made available and the retina protective diaphragm is switched into the illuminating beam path.

Figure 7:
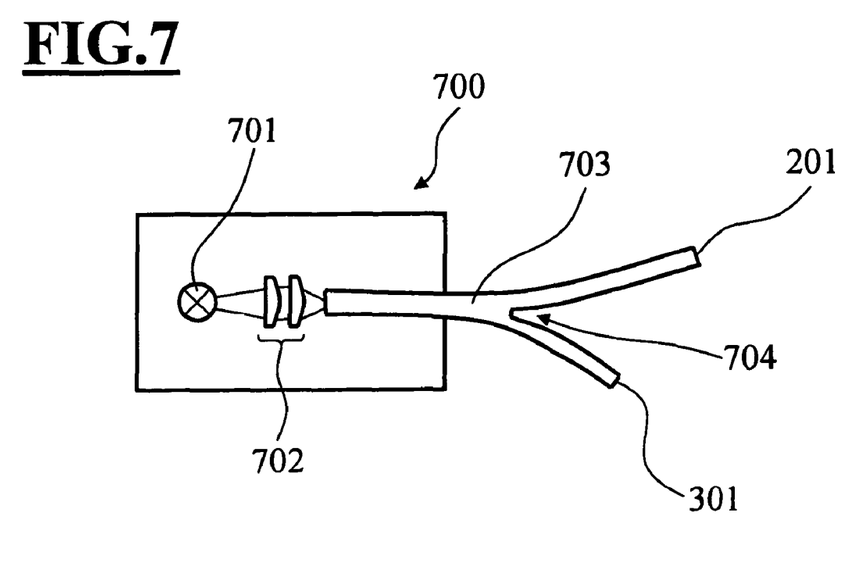
FIG. 7 shows a light conductor with a light source for supplying the illuminating arrangement of the surgical microscope with light.

A light source 700 is assigned to the illuminating arrangement 110 of the surgical microscope 100 of FIG. 1. This light source 700 is shown in FIG. 7. The light source 700 includes a halogen lamp 701 whose light is supplied to a light conductor 703 via an optic unit 702. However, it is especially also possible to provide a xenon lamp in the light source for light generation. It is noted that, as a light source, also a light source based on LEDs can be used. The light conductor 703 has a branch 704 to provide illuminating light for axis-far illumination at a first exit end 201. The light conductor has a second exit end 301 from which light for axis-near illumination of the object region exits in the surgical microscope 100 of FIG. 1.

Figure 8:
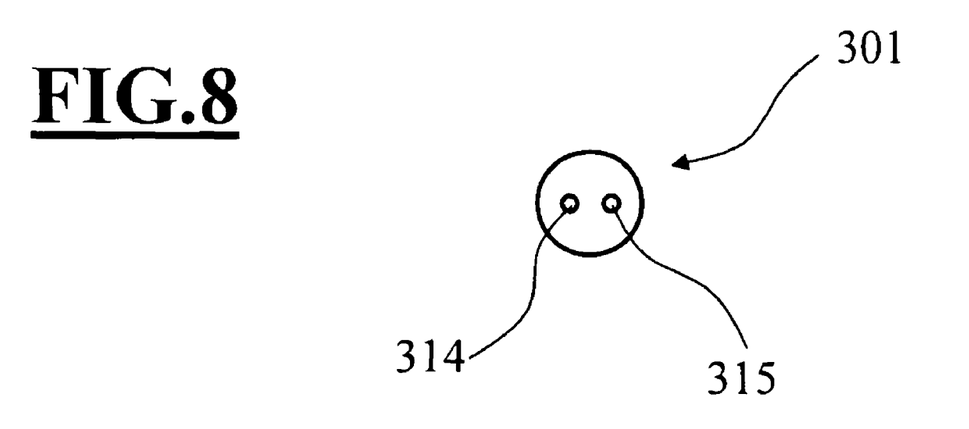
FIG. 8 shows a first exit end of the light conductor for light having two illuminating pupils.

FIG. 8 shows the exit end 301 of the light conductor 703. Exit end 301 is configured as a light exit unit having a first illuminating pupil 314 and a second illuminating pupil 315.

Figure 9:
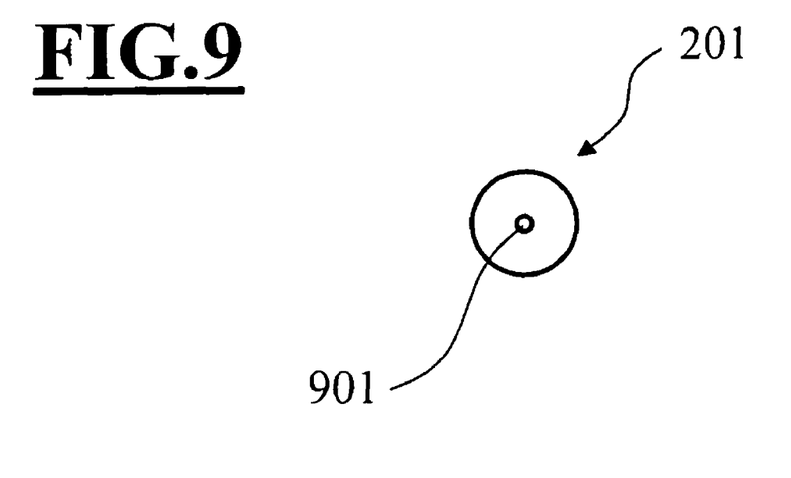
FIG. 9 shows a second exit end of the light conductor for light having a single illuminating pupil.

FIG. 9 shows the exit end 201 of the light conductor 703. The exit end 201 likewise acts a light exit unit. Here, only one illuminating pupil 901 is, however, provided.

The illuminating arrangement 110 of the surgical microscope 100 shown in FIG. 1 makes possible a most versatile illumination of the object region 105 of the surgical microscope 100. By adjusting the diaphragm 302 of FIG. 3 in the illuminating beam path 111 for axis-near illuminating light, the brightness of a red reflex produced at a patient eye can be adjusted. The diaphragm 302 is so placed in the illuminating beam path 111 of surgical microscope 100 that the illuminating field becomes uniformly darker when closing the diaphragm 302 without causing a one-sided shading or a reduction of the illuminating field diameter.

The beam path 112 for axis-far illuminating light can be attenuated by means of the diaphragm 205 of FIG. 2 in the beam path 112 and, as required, this beam path can be completely interrupted. The diaphragm 205 is, in turn, so placed in the beam path 112 that the illuminating field becomes uniformly darker without there being a one-sided shading or that the illuminating field diameter is thereby reduced. The illuminating field is caused by beam path 112 in the object region 105 of the surgical microscope.

The illumination of the object region exclusively with axis-near illuminating light from the illuminating beam path 111 of FIG. 1 is especially advantageous when using video documentation systems. When no axis-far illuminating light reaches the object region, the situation is avoided at the patient eye that excessive light is scattered at the sclera of the eye. This has the consequence of a good image contrast and the situation is avoided that images of the patient eye are too dark and too poor with respect to contrast in the region of the pupil thereof. These images of the patient eye are detected based on an automatic setting of the exposure or detected because of amplification by means of a camera.

It is understood that also electrical drives can be used for moving the adjustable diaphragms in the surgical microscope. It is also possible to design the diaphragms for the control with separate operator-controlled elements.

Figure 10:
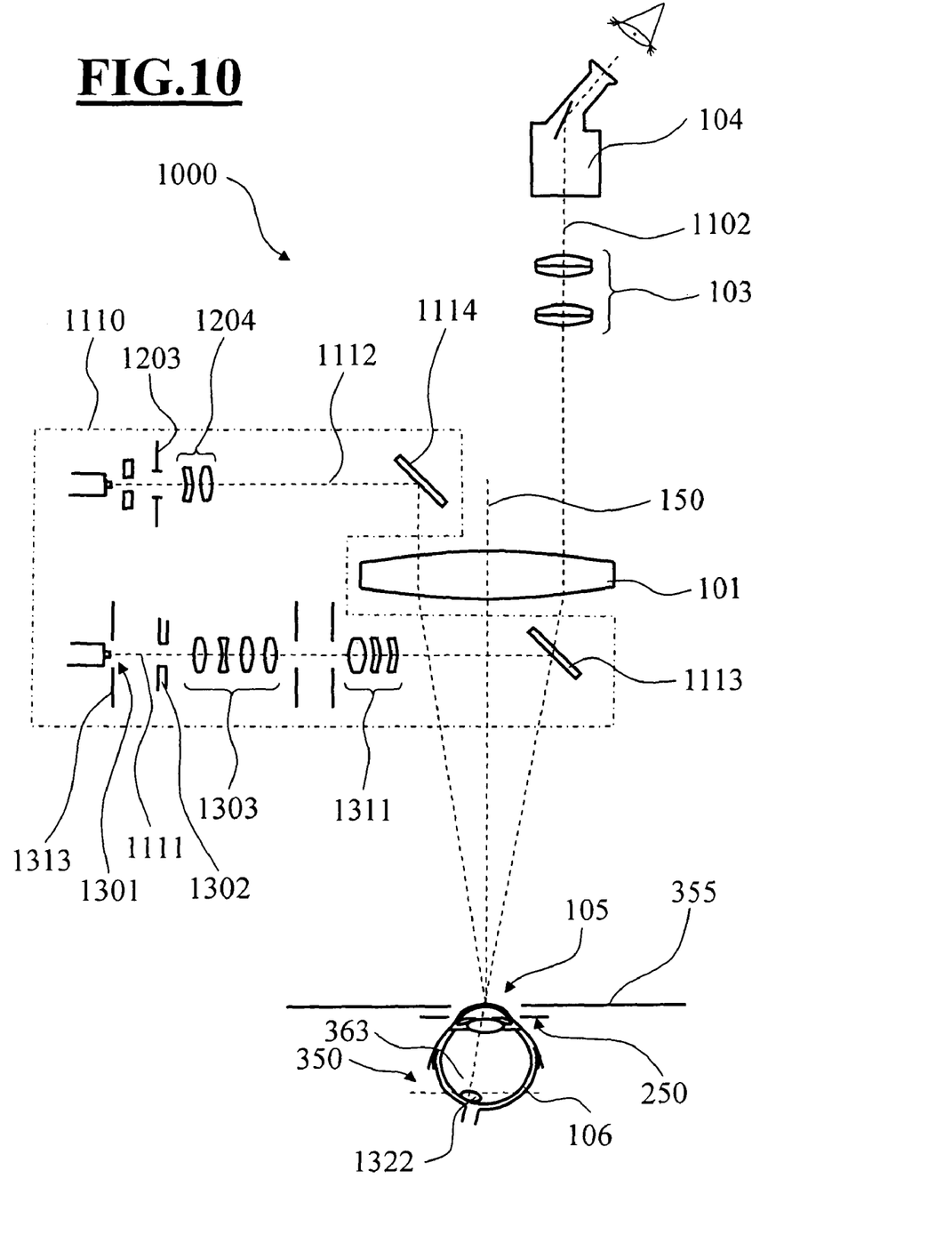
FIG. 10 is a schematic section view of a second surgical microscope having an illuminating arrangement which provides a first illuminating beam path with axis-near illuminating light which is guided past the microscope main objective to the object region and which includes a second illuminating beam path which passes through the microscope main objective.

FIG. 10 shows a further surgical microscope 1000. Component assemblies in the surgical microscope 1000 are identified by the same reference numerals as shown for the component assemblies of the surgical microscope 100 of FIG. 1 insofar as they are identical. The surgical microscope 1000 is, in turn, designed as an ophthalmologic surgical microscope and is suitable especially for examining a patient eye 106 arranged in an object region 105. In the surgical microscope 1000 in FIG. 10, the object plane 355 lies in the region of the cornea 361 of the patient eye 106, that is, the surgical microscope is focused to the cornea of the patient eye.

With respect to the stereoscopic viewing beam path 102, the surgical microscope 1000 comprises an illuminating arrangement 1110 which makes available a first illuminating beam path 1111 for axis-near illumination and a second illuminating beam path 1112 for axis-far illumination of the object region.

The illuminating arrangement 1110 includes a mirror 1113, which is partially transmissive for light and operates as a first deflecting element in order to superpose illuminating light on the stereoscopic viewing beam path 102 on the side of the microscope main objective 101 which side faces toward the object. The illuminating arrangement 1110 comprises a mirror 1114 as a second deflecting element which directs the axis-far illuminating light through the microscope main objective 101 to the object region 105.

It is noted that the principal configuration of the illuminating arrangement 1110 corresponds to that of the illuminating arrangement 110 of FIG. 1. Via an illuminating optic (1303, 1311) in the illuminating arrangement 1110, a light exit unit 1301 in a light exit plane 1313 in the first illuminating beam path 1111 is imaged in a first image plane 350 by an adjustable aperture diaphragm 1302. The second illuminating beam path 1112 contains an illuminating field diaphragm 1203 which is imaged through the microscope main objective into a second image plane 250 different from the first image plane 350 via an illuminating optic 1204. The illuminating optic (1302, 1303, 1311) is so designed that an illuminating spot 1322 is generated on the retina 363 of the patient eye 106 and the diameter of the illuminating spot 1322 lies in the range of 0.5 mm to 1.5 mm.

Figure 11:
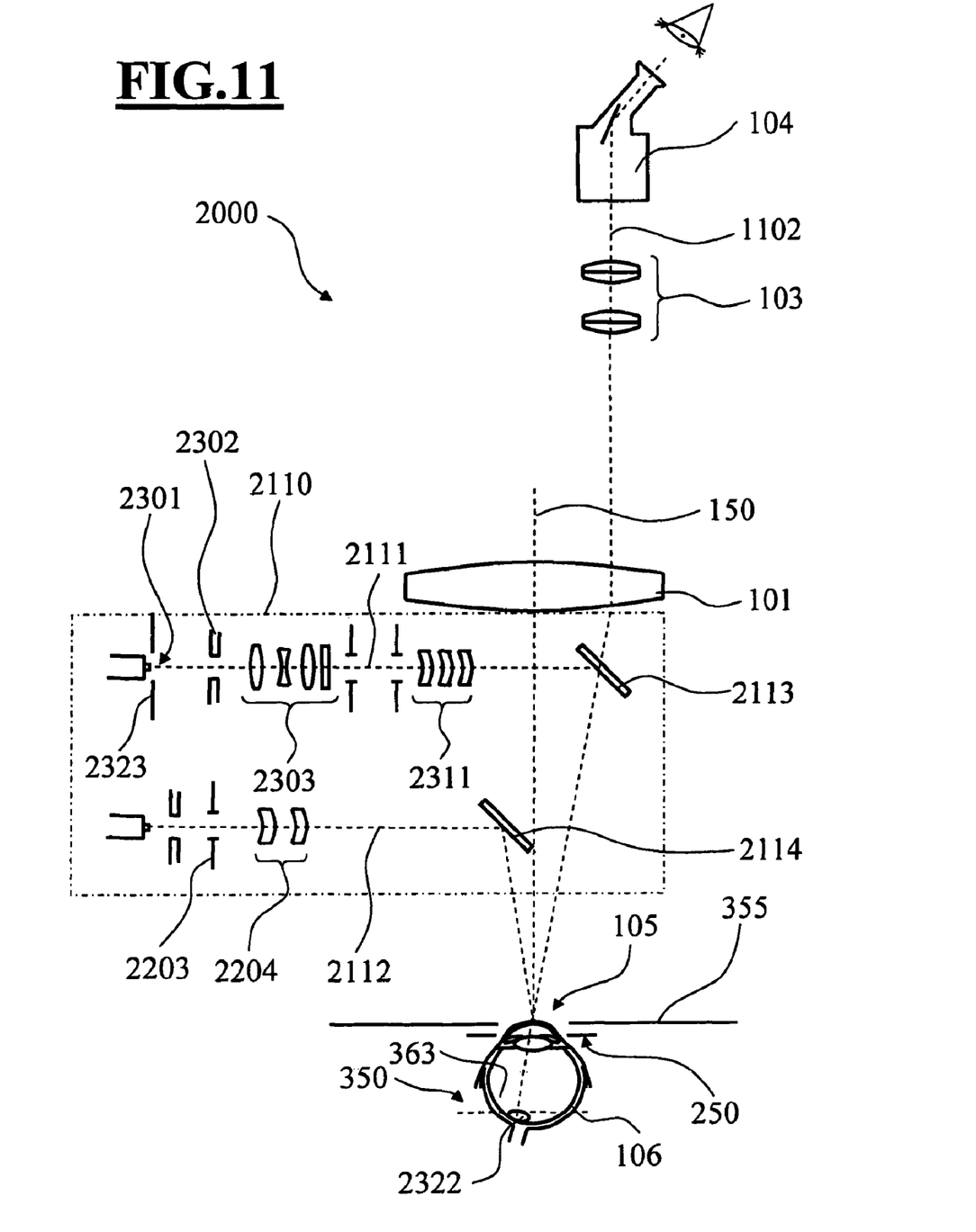
FIG. 11 is a schematic section view of a third surgical microscope having an illuminating arrangement wherein a first illuminating beam path with axis-near illuminating light is guided past the microscope main objective to the object region; and, FIG. 12 is a schematic section view of a fourth surgical microscope having an illuminating arrangement wherein a first illuminating beam path with axis-near illuminating light is guided through the microscope main objective to the object region and a second illuminating beam path provides axis-far illuminating light for the object region which is guided past the microscope main objective.

A further surgical microscope is shown in FIG. 11. The surgical microscope 2000 in FIG. 11 has a microscope main objective 101 with an optical axis 150 corresponding to the surgical microscope 1000 of FIG. 10. A stereoscopic viewing beam path 102 passes through the microscope main objective 101. The surgical microscope 2000 enables a viewer to examine an object region 105 in an object plane 355 via a magnification system 103 and a binocular tube 104. The surgical microscope 2000 is likewise designed as an ophthalmologic surgical microscope for the examination of a patient eye 106.

The surgical microscope 2000 comprises an illuminating arrangement 2110 which, with respect to the stereoscopic viewing beam path 102, makes available a first illuminating beam path 2111 for axis-near illumination and a second illuminating beam path 2112 for axis-far illumination of the object region.

The illuminating arrangement 2110 includes a mirror 2113, which is partially transmissive for light. The mirror 2113 operates a first deflecting element in order to superpose illuminating light onto the stereoscopic viewing beam path 102 on the side of the microscope main objective 101 facing toward the object. The illuminating arrangement 2110 comprises a mirror 2114 as a second deflecting element which deflects axis-far illuminating light past the microscope main objective 101 to the object region 105. It is noted that the operation of the illuminating arrangement 2110 corresponds to that of the illuminating arrangement 110 of FIG. 1 and the illuminating arrangement 1110 of FIG. 10. By means of the illuminating optic (2303, 2311) in the illuminating arrangement 2110, a light exit unit 2301 with a light exit plane 2323 in the first illuminating beam path 2111 is imaged by an adjustable aperture diaphragm 2302 into a first image plane 350. The second illuminating beam path 2112 contains an illuminating field diaphragm 2203 which, in turn, is imaged into a second image plane 250 different from the first image plane 350 by an illuminating optic 2204. The illuminating optic (2302, 2303, 2311) in the first illuminating beam path is likewise so designed that an illuminating spot 2322 is generated on the retina 363 of the patient 106. The diameter of the illuminating spot 2322 lies in a range of 0.5 mm to 1.5 mm.

Figure 12:
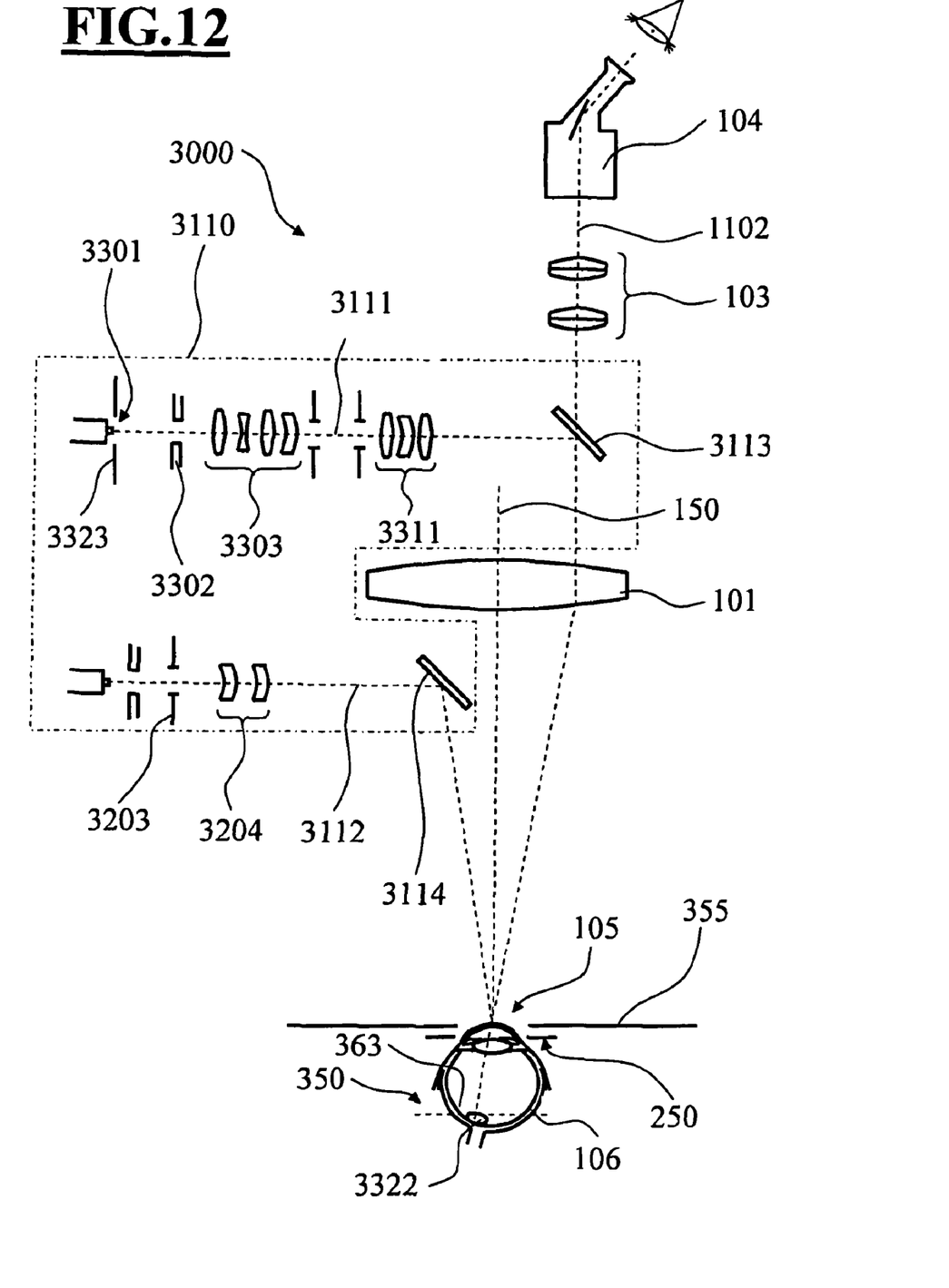

FIG. 12 shows a surgical microscope 3000. The surgical microscope 3000 has a microscope main objective 101 having an optical axis 150. The stereoscopic viewing beam path 102 passes through the microscope main objective 101. The surgical microscope 3000 makes it possible for a viewer to examine an object region 105 in an object plane 355 via a magnification system 103 and a binocular tube 104. The surgical microscope is likewise designed as an ophthalmologic surgical microscope and is suitable especially for examining a patient eye 106.

The surgical microscope 3000, in turn, comprises an illuminating arrangement 3110 as in the surgical microscopes described above. With reference to the stereoscopic viewing beam path 102, the illuminating arrangement 3110 makes available a first illuminating beam path 3111 for axis-near illumination of the object region and a second illuminating beam path 3112 for axis-far illumination of the object region.

The illuminating arrangement 3110 comprises a mirror 3113 which is partially transmissive for light. The mirror 3113 functions as a first deflecting element in order to superpose illuminating light onto the stereoscopic viewing beam path 102 through the microscope main objective 101. The illuminating arrangement 3110 comprises a mirror 3114 as a second deflecting element which directs axis-far illuminating light past the microscope main objective 101 to the object region 105.

As in the surgical microscopes 100, 1000 and 2000 of FIGS. 1, 10 and 11, respectively, a light exit unit 3301 having a light exit plane 3323 in the first illuminating beam path 3111 is imaged into a first image plane 350 in the surgical microscope 3000 of FIG. 12. The second illuminating beam path 3112 contains an illuminating field diaphragm 3203 which, in turn, is imaged by an illuminating optic 3204 into a second image plane 250 different from the first image plane 350. The illuminating optic 3302, 3303, 3311 and 101 in the first illuminating beam path 3111 of the illuminating arrangement 3110 is so designed that an illuminating spot 3322 is generated on the retina 363 of the patient eye 106. The diameter of the illuminating spot 3322 lies in the range of 0.5 mm to 1.5 mm.

In the surgical microscopes described, a good homogeneous and contrast-rich red reflex is obtained on a patient eye in that the optical axes of the viewing beam paths of the surgical microscope lie at the ocular fundus of the patient eye close to or in an optical axis of the first illuminating beam path.

It is ensured that in the left and right viewing beam paths of the surgical microscope, a red reflex of like value is visible in that a first illuminating beam path is made available which has an optical axis which, in turn, runs close to the optical axes of the viewing beam paths or runs in the optical axes of the viewing beam paths.

It is noted that it is advantageous to provide a first illuminating beam path in a surgical microscope having several stereoscopic viewing beam paths, with a stereoscopic viewing beam path for main viewing and with a stereoscopic viewing beam path for viewing by another person. This first illuminating beam path provides illuminating light which is guided to the object region with several optical axes which axes correspond to the optical axes of the viewing beam paths. In this way, a good homogeneous contrast-rich image of the anterior portion of the patient eye can be made visible with red reflex in all viewing beam paths of a surgical microscope.

It is understood that the foregoing description is that of the preferred embodiments of the invention and that various changes and modifications may be made thereto without departing from the spirit and scope of the invention as defined in the appended claims.

What is claimed is:

1. A surgical microscope for examining a region of an object, the surgical microscope comprising an illuminating arrangement including:
   a first illuminating beam path for providing illuminating light to said region of said object;
   a second illuminating beam path for providing illuminating light to said region of said object;
   a first light exit unit for making light available in said first illuminating beam path;
   an illuminating field diaphragm arranged in said second illuminating beam path;
   said first light exit unit defining a light exit plane;
   a first illuminating optic disposed in said first illuminating beam path for imaging said light exit plane or a plane conjugated to said light exit plane into a first image plane; and,
   a second illuminating optic disposed in said second illuminating beam path for imaging said illuminating field diaphragm into a second image plane different from said first image plane.

2. The surgical microscope of claim 1, wherein said surgical microscope includes a viewing beam path defining an optical axis; and, said first illuminating beam path is guided to said region of said object along an axis-near course relative to said optical axis.

3. The surgical microscope of claim 2, wherein said second illuminating beam path is guided to said region of said object along an axis-far course relative to said optical axis.

4. The surgical microscope of claim 3, wherein said surgical microscope further includes a microscope main objective arranged along said optical axis; and, said first illuminating beam path passes through said microscope main objective.

5. The surgical microscope of claim 4, said illuminating arrangement further comprising a first deflecting element for directing the illuminating light through said microscope main objective.

6. The surgical microscope of claim 5, said first deflecting element being configured as a partially transmitting mirror and being mounted so as to permit said viewing beam path to pass therethrough.

7. The surgical microscope of claim 6, wherein said partially transmitting mirror is configured as a physical beam splitter or as a geometric beam splitter.

8. The surgical microscope of claim 5, wherein said viewing beam path is a stereoscopic viewing beam path; and, said first deflecting element superposes illuminating light coaxially onto said stereoscopic viewing beam path.

9. The surgical microscope of claim 8, wherein said stereoscopic viewing beam path includes left and right viewing beam paths and said first deflecting element superposes illuminating light coaxially on each of said left and right viewing beam paths.

10. The surgical microscope of claim 4, said illuminating arrangement further comprising a second deflecting element for directing illuminating light through said microscope main objective to said region of said object.

11. The surgical microscope of claim 10, wherein said surgical microscope defines an object plane and said second image plane lies close to said object plane or is coincident with said object plane.

12. The surgical microscope of claim 1, wherein said illuminating arrangement comprises an additional diaphragm arranged adjacent said illuminating field diaphragm.

13. The surgical microscope of claim 12, wherein said additional diaphragm has an aperture that can be varied.

14. The surgical microscope of claim 13, wherein said additional diaphragm is configured as a retina protective diaphragm.

15. The surgical microscope of claim 1, wherein said illuminating arrangement further comprises an aperture diaphragm disposed in said second illuminating beam path.

16. The surgical microscope of claim 15, wherein said aperture diaphragm has an adjustable aperture.

17. The surgical microscope of claim 1, wherein said illuminating arrangement further comprises a diaphragm disposed in said first illuminating beam path; and, said diaphragm disposed in said first illuminating beam path has a fixedly variable aperture in order to change the light quantity in said first illuminating beam path.

18. The surgical microscope of claim 17, wherein said illuminating arrangement comprises: an additional diaphragm arranged in said second illuminating beam path adjacent said illuminating field diaphragm and said additional diaphragm having an aperture that can be varied; and, an aperture diaphragm also disposed in said second illuminating beam path and having an adjustable aperture; and, said illuminating arrangement further comprising a common operator-controlled element for adjusting said additional diaphragm and/or said aperture diaphragm and/or said diaphragm disposed in said first illuminating beam path.

19. The surgical microscope of claim 18, wherein said operator-controlled element is configured as a rotary knob.

20. The surgical microscope of claim 19, wherein said illuminating arrangement further comprises a shaft and actuator assembly coupled to said rotary knob; and, said shaft and actuator assembly includes: a first control cam and a first output unit operatively connected to said diaphragm disposed in said first illuminating beam path; a second control cam and a second output unit operatively connected to said additional diaphragm arranged in said second illuminating beam path; and, a third control cam and a third output unit operatively connected to said aperture diaphragm also disposed in said second illuminating beam path.

21. The surgical microscope of claim 1, said illuminating arrangement further comprising a common light source assigned to said first and second illuminating beam paths.

22. The surgical microscope of claim 21, wherein said illuminating arrangement further comprises a branched light conductor for conducting the light from said common light source to said first and second illuminating beam paths.

23. The surgical microscope of claim 22, wherein said light conductor defines said first light exit unit and comprises a second light exit unit.

24. The surgical microscope of claim 1, wherein said first light exit unit includes a first illuminating pupil and a second illuminating pupil.

25. The surgical microscope of claim 23, said illuminating arrangement comprising a single illuminating pupil formed on said second light exit unit.

26. The surgical microscope of claim 2, said illuminating arrangement further comprising a reflex diaphragm disposed in said first illuminating beam path for shading or occluding those illuminating rays which cause disturbing scattered light in said viewing beam path because of reflections on optical elements of said surgical microscope.

27. The surgical microscope of claim 26, wherein said reflex diaphragm is so arranged that no viewing rays in said surgical microscope are shaded and no cropping of said image of said illuminating field diaphragm in said second image plane is caused by said reflex diaphragm.

28. The surgical microscope of claim 1, wherein said illuminating arrangement is so configured that with illuminating light from said first illuminating beam path an illuminating spot can be generated on the retina of an ideal patient eye with said illuminating spot having a diameter lying in a range of 0.5 mm to 1.5 mm.

29. The surgical microscope of claim 28, wherein said illuminating arrangement is so configured that with illuminating light from said first illuminating beam path two illuminating spots can be generated on the retina of an ideal patient eye with said illuminating spots each having a diameter lying in said range of 0.5 mm to 1.5 mm.

* * * * *